US00PP18190P2

(12) United States Plant Patent
Sanders

(10) Patent No.: US PP18,190 P2
(45) Date of Patent: Nov. 6, 2007

(54) **NEW GUINEA *IMPATIENS* PLANT NAMED 'INGMULSCA'**

(50) Latin Name: *Impatiens hawkeri*
Varietal Denomination: Ingmulsca

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/436,808
(22) Filed: May 18, 2006
(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

PP14,170 P2 * 9/2003 Kientzler ..... Plt./318

OTHER PUBLICATIONS

UPOV ROM GTITM Computer Database, GTI Jouve Retrieval Software Citation for Ingmulsca.*

* cited by examiner

*Primary Examiner*—Wendy C. Haas
(74) *Attorney, Agent, or Firm*—Bruce Vrana

(57) ABSTRACT

A new and distinct cultivar of New Guinea *Impatiens* plant named 'Ingmulsca' characterized by its small scarlet flowers, very early flowering and very floriferous, with small foliage, good heat tolerance, nice spreading growth habit with excellent basal branching and good vigor.

1 Drawing Sheet

Latin name of the genus and species of the plant claimed: *Impatiens hawkeri.*

Varietal denomination: 'Ingmulsca'.

BACKGROUND OF THE NEW PLANT

The present invention comprises a new and distinct New Guinea *Impatiens* plant botanically known as *Impatiens hawkeri* and referred to by the cultivar name 'Ingmulsca.'

The new cultivar was developed in a controlled breeding program conducted by the inventor in Enkhuizen, Netherlands. The new New Guinea *Impatiens* cultivar is very floriferous with small flowers and small foliage, early flowering on compact, spreading plant with good heat tolerance.

The new cultivar is propagated from cuttings resulting from the cross in September 1999 of the proprietary New Guinea *Impatiens* selection identified as 'F 22-1' as female parent and the proprietary New Guinea *Impatiens* selection identified as 'F 22-2' as male parent. 'F 21-1' is not commercially available and has not been patented. 'F 22-2' is not commercially available and has not been patented.

As a result of this cross the present cultivar was selected in September 2000 in Enkhuizen, Netherlands and has been repeatedly asexually reproduced by cuttings in Enkhuizen, Netherlands, in Gilroy, Calif., and in Angers, France over a period of several years. The distinctive characteristics of this new *Impatiens* are stable and reproduced true to type in successive generations of asexual reproduction. It takes 6 to 8 weeks to produce a finished plant, starting from a rooted plug and planted in a 12 cm pot, depending on the temperature.

SUMMARY OF THE INVENTION

The following traits have been repeatedly observed and are determined to be the unique characteristics of 'Ingmulsca.' These characteristics in combination distinguish 'Ingmulsca' as a new and distinct New Guinea *Impatiens* cultivar:

1. Small, scarlet flowers
2. Very early flowering with very floriferous habit
3. Small foliage
4. Compact, spreading habit and good heat tolerance Plants of the new New Guinea *Impatiens* differ primarily from the plants of the female parent selection in the following characteristic:

Plants of the New Guinea *Impatiens* have small flowers, whereas the plants of the female parent selection have medium sized flowers.

Plants of the new New Guinea *Impatiens* differ primarily from the plants of the male parent selection in the following characteristic:

Plants of the New Guinea *Impatiens* have small flowers, whereas the plants of the male parent selection have medium sized flowers.

Plants of the new New Guinea *Impatiens* can be compared to plants of 'Kimpque,' U.S. Pat. No. 14,170. In side-by-side comparisons conducted in Enkhuizen, Netherlands, plants of the new New Guinea *Impatiens* differed from plants of the cultivar 'Kimpque' in the following characteristics:

1. Plants of the new New Guinea *Impatiens* have a more spreading habit, whereas the plants of the cultivar 'Kimpque' have a more upright growing habit.
2. Plants of the new New Guinea *Impatiens* have bright green leaves, whereas the plants of 'Kimpque' have dark green leaves.
3. Plant of the new New Guinea *Impatiens* have scarlet flowers, whereas plants of 'Kimpque' have red flowers.

DESCRIPTION OF THE DRAWING

This new New Guinea *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new New Guinea *Impatiens*. The data which defines these characteristics were collected from asexual reproductions carried out in Enkhuizen, Netherlands. The plant history was taken on 30 week old plants, blossomed under natural light in the field.

Color readings were taken in the laboratory under ambient light. Color references are primarily to The R.H.S. Color Chart of The Royal Horticultural Society of London.

The plant:
*Classification.*—Botanical: *Impatiens hawkeri.*
Parentage:
*Female parent.*—Proprietary *Impatiens hawkeri* selection identified as code number 'F 22-1,' not patented.
*Male parent.*—Proprietary *Impatiens hawkeri* selection identified as code number 'F 22-2,' not patented.
Propagation:
*Type cutting.*—Terminal cuttings.
*Time to initiate roots.*—Approximately 7–14 days.
*Time to produce a rooted cutting.*—Approximately 21 days.
*Root description.*—Fine, fibrous, and white in color.
Plant description:
*General appearance.*—Outwardly spreading, low rounded and uniform mounded plant growth.
Habit:
*Growth and branching habit.*—Compact and spreading, freely branching habit, freely flowering.
Crop time:
*Plant height.*—16 cm.
*Plant spread.*—38 cm.
Lateral branch description:
*Length.*—13–15 cm.
*Diameter.*—0.4 mm.
*Texture.*—Smooth, glabrous.
*Internode length.*—0.9–5.3 cm.
*Color.*—RHS 183A and 146D.
Foliage description:
*Arrangement.*—Primarily in whorls.
*Length, mature leaves.*—5.1 cm.
*Width, mature leaves.*—1.4 cm.
*Shape.*—Lanceolate.
*Apex.*—Acuminate.
*Base.*—Attenuate.
*Margin.*—Serrulate with fine cilation.
*Texture.*—Smooth, glabrous.
*Venation pattern.*—Pinnate.
*Color young foliage, upper surface.*—RHS 147A.
*Color young foliage, lower surface.*—RHS 194B.
*Fully expanded foliage, upper surface.*—RHS 147A.
*Fully expanded foliage, lower surface.*—RHS 194B.
*Venation, upper surface.*—RHS 185A, Anthocyanin may be present: RHS 185A.
*Venation, lower surface.*—RHS 185A, Anthocyanin may be present: RHS 185A.
*Petiole length.*—About 0.3 cm.
*Petiole diameter.*—About 0.15–0.25 mm.
*Texture.*—Smooth, glabrous.
*Color.*—RHS 185A.
Flower description:
*Flower type and flowering habit.*—Single.
*Number of flowers per leaf axil.*—1.
*Number of flowers and flower buds per lateral branch.*—10.
*Flower position.*—Above and beyond the foliage and typically facing upwards and outward.
*Flower shape.*—Rounded, mostly flat.
*Flower lasting.*—About 10 days on the plant depending on environmental conditions.
*Petals.*—Self cleaning.
*Gynoecium.*—Persistent.
*Flowers.*—Not fragrant.
*Flowering.*—Indeterminate and continuous.
*Flowering season.*—Year round under greenhouse conditions. In the garden, flowering from spring until fall.
*Flower length.*—About 4.5 cm.
*Flower width.*—About 4.5 cm.
*Flower depth.*—About 0.6 cm.
Flower buds:
*Bud length.*—About 1.2 cm.
*Bud diameter.*—About 0.4 cm.
*Bud shape.*—Ellipsoidal.
*Texture.*—Smooth, glabrous.
*Color, just before opening.*—RHS 185A.
Petals:
*Quantity.*—Single, five per flower, imbricate.
*Length of banner petal.*—About 2.2 cm.
*Width of banner petal.*—About 2.7 cm.
*Length lateral and basal petals.*—About 2.5 cm.
*Width lateral and basal petals.*—About 2.5 cm.
*Lateral and basal petal shape.*—Cordate.
*Banner petal shape.*—Roughly cordate.
*Petal apex.*—Emarginate.
*Petal base.*—Attenuate.
*Petal margin.*—Entire.
*Petal texture.*—Smooth, satiny.
*Petal color.*—Upper surface: When opening and fully opened: RHS 44B. Lower surface: When opening and fully opened: RHS N30A.
Spur:
*Length.*—About 3.2 cm.
*Texture.*—Smooth, glabrous.
*Aspect.*—Curved.
*Color.*—RHS 59A.
Peduncles:
*Length.*—About 4.5 cm.
*Strength.*—Strong, flexible.
*Diameter.*—0.1 cm.
*Aspect.*—About 45° from the stem.
*Color.*—RHS 185A.
Reproductive organs:
*Androecium.*—Stamen number: Five fused at anthers, filaments free, hooded.
*Anther shape.*—Obovate.
*Anther length.*—About 4 mm.
*Anther color.*—RHS 46B.
*Amount of pollen.*—Scarce to moderate.
*Pollen color.*—RHS 10D.
Gynoecium:
*Pistil number.*—One.
*Pistil length.*—About 3 mm.
*Stigma shape.*—Columnar, five segmented.
*Stigma color.*—Colorless.
*Style color.*—RHS 187A.
*Ovary arrangement.*—Five celled.
*Ovary color.*—RHS 187A.
Seed development: Seed development has not been observed.
Disease and pest resistance: Resistance to pathogens and pests common to *Impatiens* has not been observed.

What is claimed is:

1. A new and distinct cultivar of New Guinea *Impatiens* plant named 'Ingmulsca', as substantially illustrated and described herein.

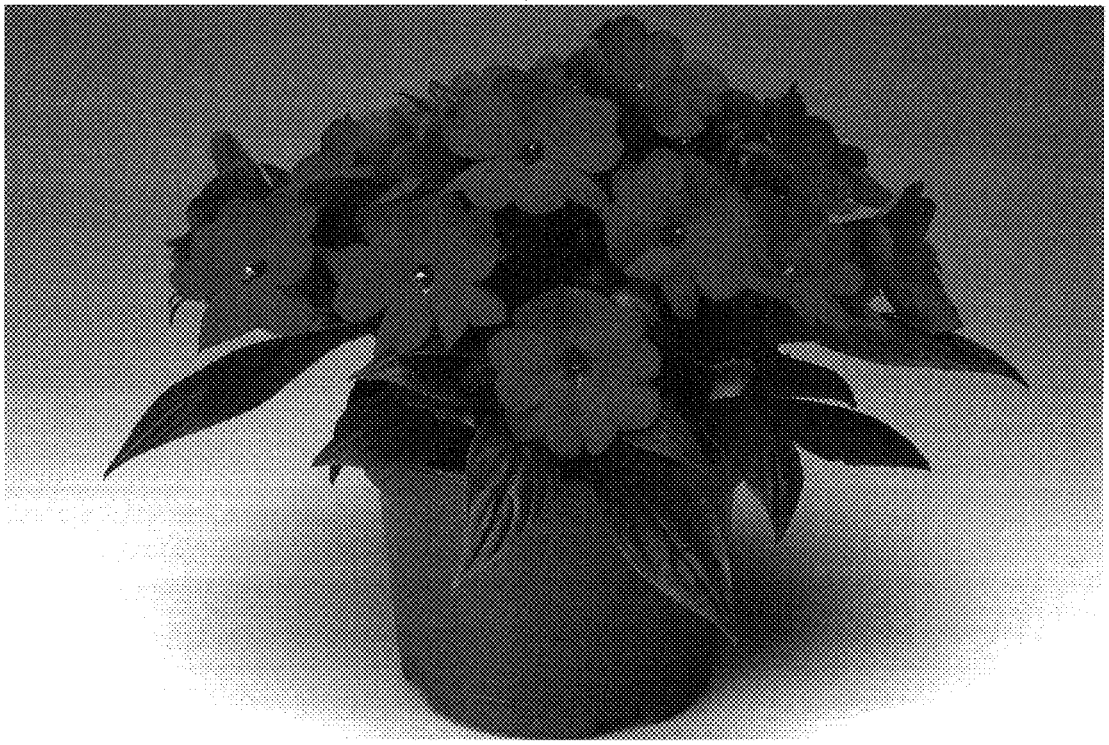

* * * * *